US008920821B2

(12) United States Patent
Avram et al.

(10) Patent No.: US 8,920,821 B2
(45) Date of Patent: Dec. 30, 2014

(54) PHARMACEUTICAL COMPOSITIONS COMPRISING SILICA MICROSPHERES

(75) Inventors: Nir Avram, Meitar (IL); Marina Shevachman, Beer-Sheva (IL); Amira Ze'evi, Omer (IL); Eilon Asculai, Lehavim (IL); Batella Binyaminovich, Beer-Sheva (IL)

(73) Assignee: Perrigo Israel Pharmaceuticals Ltd. (IL)

( * ) Notice: Subject to any disclaimer, the term of this patent is extended or adjusted under 35 U.S.C. 154(b) by 129 days.

(21) Appl. No.: 11/783,895

(22) Filed: Apr. 12, 2007

(65) Prior Publication Data

US 2007/0259013 A1 Nov. 8, 2007

Related U.S. Application Data

(60) Provisional application No. 60/791,902, filed on Apr. 14, 2006, provisional application No. 60/817,247, filed on Jun. 29, 2006.

(51) Int. Cl.

| | |
|---|---|
| ***A61K 31/203*** | (2006.01) |
| ***A61K 31/192*** | (2006.01) |
| ***A61K 9/22*** | (2006.01) |
| ***A61K 47/02*** | (2006.01) |
| ***A61K 9/00*** | (2006.01) |
| ***A61K 9/06*** | (2006.01) |

(52) U.S. Cl.

CPC ............... *A61K 47/02* (2013.01); *A61K 9/0014* (2013.01); *A61K 9/06* (2013.01); *A61K 31/192* (2013.01); *A61K 31/203* (2013.01)

USPC ............ 424/401; 424/468; 514/568; 514/559

(58) Field of Classification Search

USPC ................................ 257/27.05, 355; 424/401

See application file for complete search history.

(56) References Cited

U.S. PATENT DOCUMENTS

| | | | | |
|---|---|---|---|---|
| 3,899,578 | A * | 8/1975 | Bird et al. | 514/462 |
| 4,690,825 | A | 9/1987 | Won | |
| 4,897,269 | A * | 1/1990 | Mezei | 424/450 |
| 5,154,922 | A * | 10/1992 | Govil et al. | 424/448 |
| 5,292,512 | A * | 3/1994 | Schaefer et al. | 424/401 |
| 5,593,680 | A | 1/1997 | Bara et al. | |
| 5,618,522 | A * | 4/1997 | Kaleta et al. | 424/60 |
| 5,728,732 | A * | 3/1998 | Corey et al. | 514/544 |
| 5,785,977 | A * | 7/1998 | Breithbarth | 424/401 |
| 5,871,754 | A * | 2/1999 | Briggs et al. | 424/401 |
| 5,891,432 | A * | 4/1999 | Hoo | 424/93.21 |
| 5,955,109 | A | 9/1999 | Won et al. | |
| 6,086,924 | A | 7/2000 | Sheridan | |
| 6,303,149 | B1 | 10/2001 | Magdassi et al. | |
| 6,413,548 | B1 | 7/2002 | Hamer et al. | |
| 6,468,509 | B2 | 10/2002 | Lapidot et al. | |
| 6,881,776 | B2 | 4/2005 | Butuc | |
| 6,894,012 | B2 | 5/2005 | Sebillotte-Arnaud et al. | |
| 2002/0064541 | A1* | 5/2002 | Lapidot et al. | 424/401 |
| 2004/0101566 | A1* | 5/2004 | Cooper et al. | 424/489 |
| 2004/0175416 | A1* | 9/2004 | Taravella et al. | 424/449 |
| 2004/0241205 | A1 | 12/2004 | Babich et al. | |
| 2006/0018966 | A1 | 1/2006 | Lin et al. | |

FOREIGN PATENT DOCUMENTS

| | | |
|---|---|---|
| JP | 03-229634 | 10/1991 |
| JP | 2001038193 | 2/2001 |
| JP | 20030286196 | 10/2003 |
| WO | WO 96/21422 | 7/1996 |
| WO | WO 2005/009604 | 2/2005 |

OTHER PUBLICATIONS

Niazi. (2004). Handbook of pharmaceutical manufacturing formulations. vol. 4. p. 135.*

Definition of the word "preform," *Webster's Ninth New Collegiate Dictionary*, p. 927 (1988).

* cited by examiner

*Primary Examiner* — Audrea Buckley

(74) *Attorney, Agent, or Firm* — Thompson Hine, L.L.P.

(57) ABSTRACT

The present invention relates to a topical composition which includes a bioactive drug formulated with silica in the form of microspheres, or drugs in a combination with the silica microspheres in an oily suspension, gel or emulsion. The topical compositions of the invention provide sustained release of a bioactive drug so as to reduce skin irritation.

19 Claims, 2 Drawing Sheets

4DM681
T10CD081
Release (μg)
100
90
80
70
60
50
40
30
20
10
0
0
1
2
3
4
5
6
7
Time(hr)

PHARMACEUTICAL COMPOSITIONS COMPRISING SILICA MICROSPHERES

CROSS REFERENCE DATA

This application claims the priority of U.S. Provisional Application No. 60/791,902, filed Apr. 14, 2006 and U.S. Provisional Application No. 60/817,247, filed Jun. 29, 2006, which are incorporated hereto by reference.

BACKGROUND OF THE INVENTION

Many topical pharmaceutical products such as solids, semisolids (ointments, creams, gels), liquids and suspensions contain ingredients which may cause irritation and various inflammation symptoms when applied to the skin or mucosa.

The severity of irritation to the susceptible user may range from subclinical to mild to severe. Typical symptoms of irritation include itching (pruritus), stinging, burning, tingling, “tightness,” erythema (redness) or edema (swelling). The irritation response may be due to the direct effect on the skin of certain topical product ingredients. Many active ingredients used in topical products are known irritants or are potentially irritating, for example, retinoids, benzoyl peroxide, 5-flurouracil, hydroquinone and the like.

Retinoids are a group of compounds consisting of vitamin A and its derivatives which are very sensitive to oxidative degradation and exposure to visible light. Retinoids are effective as keratolytic agents. They are used topically to retard and ameliorate photoaging of facial skin, to treat actinic keratosis, acne vulgaris, psoriasis and warts. The main drawback of retinoids topical products, and more particularly of products including tretinoin, is skin irritation.

Hydroquinone is a reduced quinone, well-recognized as a skin-lightening agent. When topically applied, it produces a reversible depigmentation of the skin by inhibiting the enzymatic oxidation of tyrosine to 3,4-dihydroxyphenylalanine, as well as suppressing other metabolic processes of melanocytes. In a clinical setting, hydroquinone is employed to treat hypermelanosis. Hydroquinone is considered an irritant in topical applications.

Benzoyl peroxide is an antibacterial agent with demonstrated activity against Propionibacterium acnes. This action, combined with the mild keratolytic effect of benzoyl peroxide is believed to be responsible for its usefulness in acne. The main side effects of benzoyl peroxide topical formulations are redness, dryness or peeling of skin, burning and itching, and swelling.

5-Fluorouracil is an antineoplastic antimetabolite. 5-Fluorouracil interferes with the synthesis of deoxyribonucleic acid (DNA) and to a lesser extent inhibits the formation of ribonucleic acid (RNA). 5-Fluorouracil is used for topical treatment of multiple actinic or solar keratoses. In the 5% strength it is also useful in the treatment of superficial basal cell carcinomas when conventional methods are impractical, such as with multiple lesions or difficult treatment sites. The use of compositions comprising 5-Fluorouracil may cause scaling, swelling, urticaria and skin rash.

Several attempts have been made to reduce the undesirable side-effects of the above active ingredients. Thus, for example Retin-A Micro® (tretinoin) 0.1% gel, Differin® (adapalene) gel, Efudex® (Valeant) (fluorouracil) solution and cream and EpiQuin™ Micro. However, none of these are products is completely satisfactory, so the search for a better product is still on.

It will be advantageous to prepare a composition for topical application having good stability, which will reduce irritation of the skin or mucosa.

SUMMARY OF THE INVENTION

In an embodiment of the invention there is provided a pharmaceutical composition for topical application comprising silica microspheres and an active ingredient in the amount of 0.01 to 15% w/w.

In another embodiment of the invention, the composition further comprises a gelling agent.

BRIEF DESCRIPTION OF THE DRAWINGS

In the following detailed description, reference will be made to the annexed drawings, in which.

DETAILED DESCRIPTION OF THE INVENTION

Figure 1:
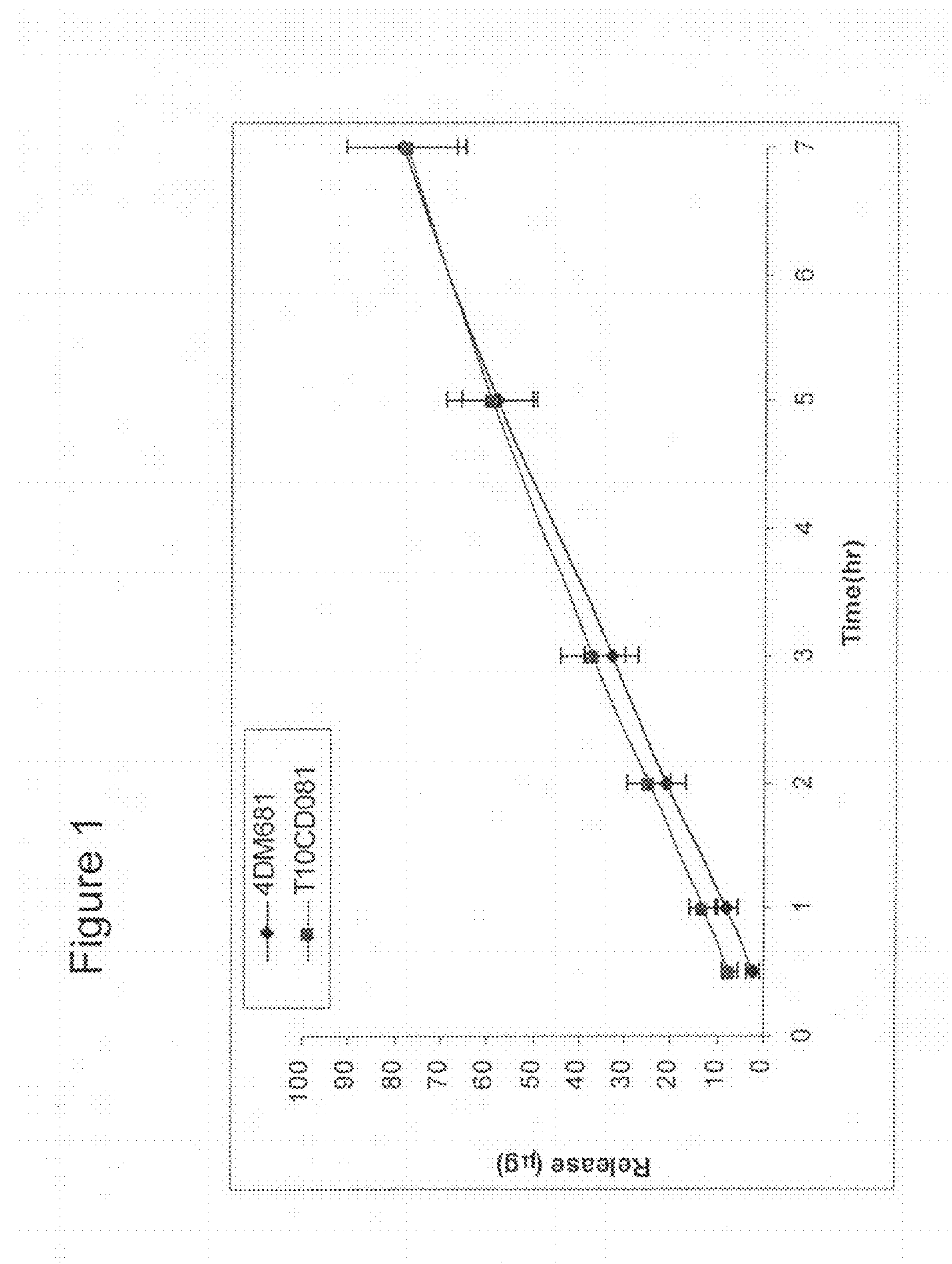
FIG. 1 is a graphical illustration of the release profile of a composition comprising tretinoin through a synthetic membrane in comparison to the release profile of Retin-A Micro gel.

The present invention provides a topical composition which releases the active ingredient in a sustained manner to so as prevent irritation or inflammation caused by the active compound. This composition may be used for skin application as well as for mucosal, nasal, and/or vaginal application.

This invention relates in general to compositions comprising silica microspheres for topical application of pharmaceuticals. Such compositions are smooth and easy to spread and provide a non-tacky, velvety after-feel due to the presence of the silica microspheres.

In an embodiment of the invention, the composition is formulated in a semisolid or a liquid form, such as for example without being limited, a gel, a cream, a lotion, a foam, a paste, an ointment, a shampoo, a suspension or a semisolid powder. In another embodiment, the composition is formed as a spray or an aerosol. In another embodiment, the composition is formed as a suppository.

In an embodiment of the invention, this invention relates to compositions for topical use comprising silica microspheres which are impregnated with an active agent.

Throughout the application, “silica microspheres” means, silicon dioxide discrete spherical particles ranging in average size from 0.5 to 40 microns.

In an embodiment of the invention, the silica microspheres may range in average size from 1 to 20 microns.

The invention is based on the observation that formulations comprising silica microspheres afford optimal release of the active ingredient, according to the embodiments of the invention.

According to some embodiments of the invention, there are provided compositions for topical application of a pharmaceutical active agent, which comprise silica microspheres with an active ingredient in amount of 0.01 to 15% w/w in a gel phase.

The active ingredient may be any active ingredient used for treating skin or other topical disorders.

In some embodiments of the invention, the active ingredient may be for example, without limitation, a vitamin, a keratolytic agent, a steroid, a non-steroidal anti-inflammatory drug, an antibiotic, a tranquilizer, an antihistaminic, an antifungal, an antibacterial, an antiviral, an anti-itching agent, a wart-treatment agent, a disinfectant, an immunosuppressant, an anticancer or a local anesthetic or combination thereof.

In an embodiment of the invention, the composition may comprise an active ingredient, which can be for example, without limitation, vitamin A, a retinoid, tretinoin, adapalene, tazarotene, hydroquinone, benzoyl peroxide, 5-fluorouracil, azelaic acid or any combination thereof.

The composition of the invention may be used to treat skin disorders and diseases, including atopic dermatitis, psoriasis, rosacea, cancer, actinic keratosis, acne, skin pigmentation and other types of skin inflammations or viral, fungal or bacterial skin infections.

Depending upon whether the active ingredient is hydrophobic or hydrophilic, it will be present in an oily or aqueous phase, respectively.

In an embodiment of the invention, the retinoids may be used for the treatment of acne. Retinoids may be also useful in treatment of skin photoaging and sun damage. Many individuals who have had a good deal of sun exposure will show the following gross cutaneous alterations: wrinkling, leatheriness, yellowing, looseness, roughness, dryness, mottling (hyperpigmentation) and various premalignant growths (often subclinical). These changes are most prominent in light-skinned persons who burn easily and tan poorly. These cumulative effects of sunlight are often referred to as "photoaging" skin.

When considering the use of retinoids in skin care products, it is believed that certain retinoids such as retinol (Vitamin A alcohol), retinal (Vitamin A aldehyde) and retinyl esters such as retinyl acetate and retinyl palmitate would be suitable.

Due to retinoids' sensitivity to light and air, and their skin irritability, much attention in topical products containing such compounds is directed toward providing a composition which has a prolonged shelf life and can deliver active ingredients in slow-release pattern, to prevent skin irritation.

In an embodiment of the invention, the composition comprises an active ingredient, which is a retinoic acid or a derivative thereof.

In another embodiment of the invention, the composition comprises active ingredient, which is tretinoin.

In an embodiment of the invention, the amount of the active ingredient is 0.04-0.3% w/w.

In an embodiment of the invention, the amount of the active ingredient is 0.075-0.125% w/w.

In an embodiment of the invention, the amount of the active ingredient is 0.1-1.0% w/w.

In an embodiment of the invention, the amount of the active ingredient is 1.0-15% w/w.

In an embodiment of the invention, the amount of the tretinoin may be between about 0.05-0.3% w/w.

In an embodiment of the invention, the active ingredient is benzoyl peroxide. The concentration of the benzoyl peroxide may range between about 3-9% w/w.

In an embodiment of the invention, the active ingredient is hydroquinone. The concentration of the hydroquinone may be about 4% w/w.

In an embodiment of the invention, the active ingredient is 5-flurouracil. The concentration of the 5-flurouracil may be between about 0.5-5% w/w.

In an embodiment of the invention, formulation may comprise about 6% to 20% of an oily phase, excluding the active ingredient.

In an embodiment of the invention, formulation may comprise about 5% to 10% of an oily phase excluding the active ingredient.

The microsphere size in the compositions of the invention is in the size range of about 0.5 to about 40 microns. In an embodiment of the invention, the size range may be of about 1 to 20 microns.

In some embodiments of the invention, the composition may comprise a gelling agent.

The gelling agent of the invention, may be without limitation, a cellulose derivative such as methyl cellulose, carboxymethyl cellulose and carboxymethyl cellulose salts, hydroxymethyl cellulose, hydroxypropyl methylcellulose (HPMC), hydroxyethyl cellulose, tri-block copolymers (Poloxamer 407, for example), xanthan gum, a carrageenan, pectin, a mannan, curdlan, chondroitin sulfate, starch, galactan, dermatan sulfate, glycogen, gum arabic, a heparan sulfate, hyaluronic acid, hyaluronate sodium, tragacanth gum, hydroxyethyl cyamoposis gum, carboxymethyl cyamoposis gum, cyamoposis gum, a dextran, keratosulfate, chitosan, a carboxymethyl chitin, an agar, etc. One or more of the above may be used in admixture, or can be blended with thickeners and/or water-soluble polymers.

In an embodiment of the invention, the gelling agent may be in an amount between 0.5-20% w/w. In another embodiment of the invention, the gelling agent may be in an amount between 5-15% w/w.

In an embodiment of the invention, the amount of the gelling agent may be 1-4% w/w. In another embodiment the amount may be 2.5% w/w.

In an embodiment of the invention the composition may further comprise solvent.

Further, the composition may comprise an antioxidant.

Further, the composition may comprise an antimicrobial preservative.

Further, the composition may comprise an emulsifier.

Further, the composition may comprise an emollient, humectant and water.

Suitable solvents include, but are not limited to alcohol, isopropanol, oleic acid, glycerol monooleate, oleyl alcohol, propylene glycol, isopropyl myristate or any combination thereof.

In some embodiments of the invention, the solvent may be in an amount of about 3 to 20%. In another embodiment, the solvent may be in an amount of about 4 to 15%. In another embodiment the solvent may be in an amount of about 6 to 10%.

In an embodiment of the invention when the solvent is oleic acid, the amount of the oleic acid may be about 2 to 10%. In another embodiment of the invention, the amount of the oleic acid is between 3 to 8%. In another embodiment the amount of the oleic acid is between 3 to 6%.

In an embodiment of the invention when the solvent, is isopropanol. The amount of the isopropanol may be about 2 to 20%. In another embodiment of the invention, the isopropanol may be in an amount of about 3 to 15%. In another embodiment the amount of the isopropanol may be between 4 to 10%. In another embodiment, the amount of the isopropanol may be between about 5-6%.

In an embodiment of the invention the active ingredient may be dissolved by combination of oleic acid and isopropanol.

In addition, compositions of the invention may also comprise conventional additives such as preservatives and antioxidants.

Typical preservatives include sorbic acid, thimerosal, benzyl alcohol, benzoic acid, chlorbutanol, maleic acid and methyl, ethyl, propyl or butyl parabens or any combination thereof.

In addition, compositions of the invention may also comprise a chelating agent of a polyamine carboxylic acid such as ethylene diamine tetraacetic acid ("EDTA"), or a pharmaceutically acceptable salt thereof.

The antioxidant may be butylated hydroxytoluene (BHT), butylated hydroxyanisole (BHA), alpha-tocopherol or alpha-tocopherol succinate, sodium ascorbate or any combination thereof.

In an embodiment of the invention, the antioxidant may be in an amount of about 0.001 to 1%. In another embodiment the antioxidant may be in an amount ranging from 0.01 to 0.1%. In another embodiment of the invention, the antioxidant may be in an amount of about 0.01 to 0.05%. In another embodiment, the amount of the antioxidant is about 0.02%.

The antimicrobial preservative should be chosen so as to fit topical administration, and one skilled in the art can conduct tests to routinely select specific antimicrobial preservative for this purpose. In an embodiment of the invention, the sorbic acid is in an amount of about 0.01 to 1%. In another embodiment the sorbic acid may be in an amount of about 0.02 to 0.5%. In another embodiment the sorbic acid may be in an amount of about 0.05 to 0.2%. In another embodiment, the amount of the sorbic acid is about 0.1%.

The antimicrobial preservative may be but is not limited to benzyl alcohol in an amount of about 0.1 to 5%. In another embodiment the amount of the benzyl alcohol may be of about 0.2 to 2%. In another embodiment the amount of the benzyl alcohol may be of about 0.5 to 1%. In another embodiment, the amount of the benzyl alcohol is about 0.8%.

Suitable emulsifiers in this embodiment include, but are not limited to, tri-block copolymers (Poloxamer 407, Poloxamer 188), Polyoxyl stearates (Polyoxyethylene-20 stearate—Mirj 49, etc), Polysorbates (Tween 80, Tween 60 and Tween 20), Sorbitane fatty acid esters (Span 60 or Span 80), POE alkyl ethers (Brij 97, etc.), POE alkylphenyl ethers (POE nonylphenyl ether, etc.), sucrose fatty acid ester.

The emulsifier may be Poloxamer 407 in an amount of about 0.2 to 5%. In another embodiment the emulsifier may be in an amount of about 0.2 to 2%. In another embodiment the emulsifier may be in an amount of about 0.5 to 1%. In another embodiment, the amount of the emulsifier is about 0.5%.

The emollient or humectant should be chosen so as to suitable for topical administration, and one skilled in the art can conduct tests to routinely select specific viscosity modifier for this purpose. Suitable emollient or humectant include, but are not limited to glycerin, propylene glycol, cyclomethicone, dimethicone copolyol or any combination thereof.

The emollient may be in an amount of about 1 to 30%. In another embodiment the amount of about 3 to 20%, preferably 4-15%.

The oily component without an active ingredient is typically present in an amount of about 10-30%, and may include oleic acid, isopropanol, BHT, sorbic acid.

In the following description and in the examples, concentrations will be indicated by wt % which denotes the concentration by weight of the component per 100 units weight of entire composition. All indicated concentrations should be understood as standing each by itself, and are not cumulative. It should be appreciated by the artisan, however, that there is some dependency between the concentrations of the components, e.g., higher concentrations of the oil will generally require higher concentrations of the emulsifier and surfactant.

In an embodiment of the invention, concentrations of the components are as follows: about 2 to 25% oily phase solvent; about 0.2 to 2% of the emulsifier, with about 0.2 to 1% being particularly preferred; about 0.01 to 1% for the antioxidant, with about 0.02 to 0.10% being particularly preferred; about 0.05 to 5% for the antimicrobial preservative, with about 0.1 to 1% being particularly preferred. For a topical gel application, about 0.2 to 15% of the gelling or thickening agent can be included.

In some embodiments of the invention there is provided a process for the preparation of a topical composition comprising silica microspheres in a gel preparation, about 0.05 to 20% w/w of a gelling agent, and an active ingredient in the amount of 0.01 to 0.5% w/w. The process comprises: mixing the gelling agent with water so as to form a gelling composition; adding emulsifier (Poloxamer 407 or Span 80) to the components of the oily phase; adding silica or silica suspended in water to the oily phase to impregnate silica microspheres with an active compound; and mixing said oily phase with the gelling composition.

The formulation process of the invention may further comprise adding preservatives and humectants to the resultant composition.

In an embodiment of the invention, the composition may comprise oleic acid 2-10% w/w, Isopropanol 2-20% w/w, Sorbic acid 0.01-1% w/w, active ingredient 0.01-10.0%, silica microspheres 0.2-5.5% w/w, carboxymethyl cellulose sodium 0.5-4.0% w/w, glycerin 3-20% w/w, benzyl alcohol 0.1-5.0% w/w, Poloxamer 407 0.2-20% w/w and purified water.

In another embodiment of the invention, the composition may comprise oleic acid 3-8% w/w, Isopropanol 3-15% w/w, butylated hydroxytoluene 0.01-0.05% w/w, sorbic acid 0.02-1.0% w/w, active ingredient 0.01-10.0%, silica microspheres 0.2-1.5% w/w, carboxymethyl cellulose sodium 1.0-3.0% w/w, benzyl alcohol 0.2-2.0% w/w, Poloxamer 407 0.2-15% w/w, glycerin 3-15% w/w, EDTA, and purified water.

In an embodiment of the invention, the composition may comprise oleic acid 4-6% w/w, isopropanol 5-10% w/w, butylated hydroxytoluene 0.01-0.03% w/w, sorbic acid 0.05-0.2% w/w, active ingredient 0.01-4% w/w, silica microspheres 0.25-1.0% w/w, carboxymethyl cellulose sodium 2.0-2.5% w/w, glycerin 3-15% w/w, benzyl alcohol 0.5-1.0% w/w, sodium hydroxide or trolamine to adjust pH and purified water.

In an embodiment of the invention, the invention is directed to a method for treating acne vulgaris, the method comprising administering an effective amount of the composition of the invention, wherein the active ingredient is tretinoin. The amount of the tretinoin may be 0.1%.

In an embodiment of the invention, the invention is directed to a method for depigmentation, the method comprising administering an effective amount of the composition of the invention, wherein the active ingredient is hydroquinone. The amount of the hydroquinone may be 4%.

In an embodiment of the invention, the invention is directed to a method for treating actinic keratoses, the method comprising administering an effective amount of the composition of the invention, wherein the active ingredient is 5-fluorouracil. The amount of the 5-fluorouracil may be 0.5-5%.

In an embodiment of the invention, the invention is directed to a method for treating actinic keratoses, the method comprising administering an effective amount of the composition of the invention, wherein the active ingredient is benzoyl peroxide. The amount of the benzoyl peroxide may be 3-12%. In an embodiment of the invention, the amount of the benzoyl peroxide is up to and including 10%.

The invention is illustrated with reference to the above-mentioned examples, which are to be construed in a strictly non-limiting manner.

EXAMPLES

Examples 1-4 are topical compositions comprising tretinoin. Ingredients amounts are in weight percentages. The compositions were prepared according to the processes described in detail in the examples below. It is noted that the following examples do not limit in any way the scope of the present invention.

Example 1

A Composition Comprising Tretinoin as an Active Ingredient

| Ingredient | Concentration (w/w %) |
|---|---|
| Oleic acid | 5.00 |
| Isopropanol | 8.00 |
| BHT (Butylated Hydroxytoluene) | 0.02 |
| Sorbic acid | 0.10 |
| Tretinoin | 0.10 |
| Silica microspheres | 0.70 |
| (l cellulose sodiumcarboxymethy) CMC Na | 2.40 |
| Glycerin | 5.00 |
| Benzyl alcohol | 0.80 |
| Poloxamer 407 | 0.50 |
| Water A .P | 70.38 |
| Water B .P | 7.00 |

The process for the preparation of the composition was carried out as follows:

1. CMC Na (carboxymethyl cellulose sodium) was added to water A and was stirred vigorously until gel was formed;
2. Glycerin and benzyl alcohol were added to stage 1 and mixed for ten minutes;
3. Oleic acid, isopropanol, BHT, sorbic acid, Poloxamer 407 and tretinoin were heated to 50° C. while stirring, until clear solution was obtained. Then the solution was cooled to room temperature;
4. Silica Microspheres in water B were added to the cooled oily phase and resultant mixture was stirred for at least one hour;
5. Stage 4 was added to the mixer and stirred for one hour under vacuum.

Figure 2:
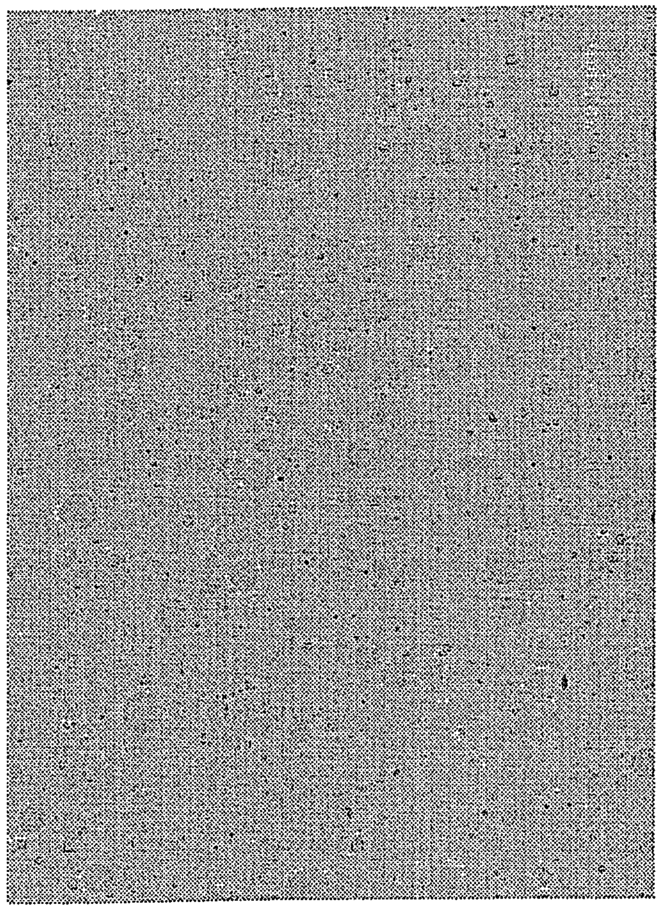
FIG. 2 shows a close-up view of a sample of the formulation including the silica microspheres and tretinoin according to Example 1.

An opaque yellowish gel was obtained. A close-up view of the formulation including the silica microspheres is attached hereto as FIG. 2.

Example 2

A Composition Comprising Tretinoin as an Active Ingredient

| INGREDIENTS | CONCENTRATION (% W/W) |
|---|---|
| Oleic acid | 4.00 |
| Isopropanol | 6.00 |
| BHT (Butylated Hydroxytoluene) | 0.02 |
| Sorbic acid | 0.10 |
| Tretinoin | 0.10 |
| Silica microspheres | 0.70 |
| Natrosol (HEC) | 1.50 |
| Xanthan gum | 0.80 |
| Trolamine | 1.20 |
| Benzyl alcohol | 0.80 |
| Glycerin | 15.00 |
| Water | q.s 100% |

-continued

The process for the preparation of the composition was as follows:

1. Trolamine, Natrosol (HEC) and xanthan gum were added gradually to the water while stirring at high speed using mixer propeller;
2. The mixture of oleic acid, isopropanol, BHT, sorbic acid and tretinoin was heated to 50° C. while stirring then cooled to the room temperature;
3. Silica microspheres were added to the stage 2 and the resultant mixture was stirred for at least one hour;
4. Benzyl alcohol and Glycerin were added to stage 1
5. Stage 4 was added to the mixer reactor and stirred vigorously.

An opaque yellowish gel was obtained.

Example 3

A Composition Comprising Tretinoin as Active Ingredient

| INGREDIENTS | CONCENTRATION (% W/W) |
|---|---|
| Oleic acid | 4.00 |
| Isopropanol | 5.00 |
| BHT (Butylated Hydroxytoluene) | 0.02 |
| Sorbic acid | 0.10 |
| Tretinoin | 0.10 |
| Silica microspheres | 0.50-1.00 |
| Poloxamer 407 A | 12.00-15.00 |
| Poloxamer 407 B | 0.2-1.0 |
| Benzyl alcohol | 0.80 |
| Glycerin | 15.00 |
| Sodium hydroxide, diluted | Adjust pH |
| Water | q.s 100% |

The process for the preparation of the composition was as follows:

1. Poloxamer 407 A was added to the water while stirring at high speed using mixer propeller;
2. The mixture of oleic acid, isopropanol, BHT, sorbic acid, Poloxamer B and tretinoin was heated to 50° C. while stirring and then was cooled to the room temperature;
3. Silica Microspheres were added to the stage 2 and resultant mixture was stirred for at least one hour;
4. Benzyl alcohol and glycerin were added to stage 1 and stirred;
5. Stage 3 was added to the mixer reactor and stirred vigorously;
6. Sodium hydroxide was added for pH adjustment.

An opaque yellowish gel was obtained.

Example 4

A Composition Comprising Tretinoin as Active Ingredient

| INGREDIENT | CONCENTRATION (% W/W) |
|---|---|
| Oleic acid | 5.00 |
| Isopropanol | 10.00 |
| BHT (Butylated Hydroxytoluene) | 0.02 |
| Sorbic acid | 0.10 |
| Tretinoin | 0.10 |
| Silica microspheres | 0.70 |
| CMC Na (carboxymethyl cellulose sodium) | 2.40 |
| Natrosol (HEC) | 0.50 |
| Glycerin | 5.00 |
| Benzyl alcohol | 0.80 |
| Poloxamer 407 | 0.20 |
| P. Water | q.s 100% |

The process for the preparation of the composition was as follows:

1. CMC Na (carboxymethyl cellulose sodium) and Natrosol (HEC) were dispersed in water until a clear gel was formed
2. Glycerin and benzyl alcohol were added to stage 1 and mixed;
3. Oleic acid, isopropanol, BHT, sorbic acid, Poloxamer 407 and tretinoin were heated to 50° C. while stirring until clear solution was obtained. Then the solution was cooled to the room temperature;
4. Silica Microspheres were added to the cooled oily phase and resultant mixture was stirred for at least one hour;
5. Stage 4 was added to the stage 2 and stirred for one hour under vacuum.

An opaque yellowish gel was obtained.

Example 5

A Composition Comprising Hydroquinone as an Active Ingredient

| INGREDIENTS | CONCENTRATION (% W/W) |
|---|---|
| Oleic acid | 3.00 |
| Isopropanol | 8.00 |
| BHT (Butylated Hydroxytoluene) | 0.02 |
| Sorbic acid | 0.10 |
| Vitamin A | 0.10 |
| Poloxamer 407 | 0.50 |
| Hydroquinone | 4.00 |
| Silica microspheres A | 1.00 |
| Silica microspheres B | 0.50 |
| Blanose - CMC | 2.00 |
| EDTA | 0.04 |
| Benzyl alcohol | 0.80 |
| Glycerin | 5.00 |
| Water A | 30.34 |
| Water B | 45.00 |

The process for the preparation of the composition was as follows:

1. To water A the following components were added: EDTA, glycerin and hydroquinone. The mixture was heated to the 60° C. under stirring, and after the mixture was clear, it was cooled to the 40° C.;
2. Silica microspheres A were added to stage 1 and stirred;
3. The mixture of oleic acid, isopropanol, BHT, sorbic acid, Poloxamer 407 and Vitamin A was heated to 50° C. while stirring until all components were dissolved;
4. Silica microspheres B were added to stage 3 and stirred;
5. Stage 4 was added to the stage 2 and stirred for at least one hour;
6. Blanose (CMC) was added to water B and stirred by using a mixer propeller for the complete dispersion;
7. Benzyl alcohol was added to stage 6;
8. Stage 7 was added to stage 5 and the mixture was homogenized.

Example 6

A Composition Comprising 10% Benzoyl Peroxide (BPO) as Active Ingredient

| INGREDIENTS | CONCENTRATION (% W/W) |
|---|---|
| Benzoyl peroxide (BPO) | 10.00 |
| Ethoxydiglycol | 19.50 |
| Glycerin | 8.00 |
| Silica microspheres | 5.50 |
| Carbomer | 0.60 |
| Imidazolidinyl Urea | 0.30 |
| PEG-40 Hydrogenated | 0.20 |
| Disodium EDTA | 0.10 |
| Sodium Hydroxide | 0.16 |
| Water | q.s 100% |

Example 7

A Composition Comprising 5% Benzoyl Peroxide (BPO) as Active Ingredient

| INGREDIENTS | CONCENTRATION (% W/W) |
|---|---|
| Benzoyl peroxide (BPO) | 5.00 |
| Ethoxydiglycol | 9.90 |
| Glycerin | 8.00 |
| Silica microspheres | 2.50 |
| Carbomer | 0.60 |
| Imidazolidinyl Urea | 0.30 |
| PEG-40 Hydrogenated | 0.20 |
| Disodium EDTA | 0.10 |
| Sodium Hydroxide | 0.16 |
| Water | q.s 100% |

The process for the preparation of the compositions listed above was as follows:

1. Disodium EDTA and Carbomer were added to the water and homogenized;
2. Glycerin was added to stage 1 and the mixture was stirred;
3. PED-40 hydrogenated castor oil was heated to 40° C. separately and after clear liquid was obtained, it was added to stage 2;
4. 20% solution of sodium hydroxide was added for neutralization;
5. A solution of imidazolidinyl urea in water was added to stage 4;
6. Benzoyl peroxide was added to ethoxydiglycol separately and passed through Fryma colloid mill, twice;

7. Silica microspheres were added to the stage 6 and resultant mixture was stirred;
8. Stage 7 was added to stage 5 and the mixture was homogenized.

Example 8

A Composition Comprising Adapalene as an Active Ingredient

| Ingredients | Concentration (% w/w) |
|---|---|
| Mineral oil | 6.00 |
| Isopropyl Myristate | 3.00 |
| BHT (Butylated Hydroxytoluene) | 0.02 |
| Sorbic acid | 0.10 |
| Adapalene | 0.10 |
| Silica microspheres | 0.70 |
| CMC Na (carboxymethyl cellulose sodium) | 2.40 |
| Poloxamer 188 | 1.00 |
| Benzyl alcohol | 0.80 |
| Propylene glycol | 10.00 |
| Water | q.s 100% |

Example 9

Release Rate of Tretinoin from the Tretinoin Gel Formulation of Example 1

To compare the release rate of Tretinoin from Retin-A Micro gel formulation versus tretinoin gel formulations with silica microspheres, an in-vitro test through a synthetic membrane (Supor 450) was performed. As is shown in FIG. 1, the release profile of the active compound from the formulation of Example 1 was identical to that of Tretinoin form Retin A-Micro formulation.

Example 10

Comparative Irritation Test in Rabbit (Draiz test

A 10-day Repeat Dermal Tolerance study in New Zealand White Rabbits is conducted to assess the dermal tolerance of tretinoin formulations (compositions of the present invention and brand) during which the invention's formulations are applied repeatedly on the skin of rabbits for ten consecutive days. A quantity of 0.5 g of each test item formulation is applied to the prepared area of skin and spread uniformly on the skin to cover an approximately 6 cm2 (2×3 cm) patch. The treated patches are then left open (un-occluded). The test item formulations are applied each morning and, after a 4 hour contact period, all the treated areas and untreated control areas are washed thoroughly with de-ionized water in order to remove the test item residue. The treatment is performed for 10 consecutive days. The skin reaction is assessed according to the numerical scoring system of Draize et. al (1944), as defined in the following tables:

1. ERYTHEMA AND ESCHAR FORMATION (Max possible score—4)

| | |
|---|---|
| No erythema | 0 |
| Very slight erythema (barely perceptible | 1 |
| Well-defined erythema | 2 |
| Moderate to severe erythema | 3 |
| Severe erythema (beef redness) to slight eschar formation (injuries in depth) | 4 |

2. EDEMA FORMATION (Max possible score—4)

| | |
|---|---|
| No edema | 0 |
| Very slight edema (barely perceptible) | 1 |
| Slight edema (edges of area well defined by definite raising) | 2 |
| Moderate edema (raised approximately 1 millimeter) | 3 |
| Severe edema (raised more than 1 millimeter and extending beyond area of exposure) | 4 |

Two methods are used to evaluate the irritation potential of the compositions of the present invention and brand:

The mean scores of all the rabbits for erythema and edema, for all ten days of treatment and three days post treatment, are added up separately, and the highest mean score is used to calculate the irritation potential of the test item.

The skin scores of all the rabbits are added up and divided by the total number of observations, to arrive at the mean; this is then used to calculate the irritation potential of the test item.

What is claimed is:

1. A sustained release composition for topical application of pharmaceuticals comprising:

preformed silica microspheres impregnated with benzoyl peroxide such that there is also free benzoyl peroxide in the composition, wherein the composition comprises at most 10 percent by weight benzoyl peroxide and silica in an amount between 0.20-5.50% w/w, and wherein said composition is formulated for sustained release of said benzoyl peroxide;

wherein the preformed silica microspheres were formed prior to being mixed with the benzoyl peroxide.

2. The sustained release composition of claim 1 having a mean microsphere size in the range of 0.5 micron to 40 microns.

3. The sustained release composition of claim 1 having a mean microsphere size in the range of 1 micron to 20 microns.

4. The sustained release composition of claim 1 further comprising a gelling agent.

5. The sustained release composition of claim 1 further comprising one or more of a solvent, an antioxidant, an antimicrobial preservative, an emulsifier, and water.

6. The sustained release composition of claim 1, wherein the composition is a gel, a cream, a lotion, a foam, a shampoo, or a suspension.

7. The sustained release composition of claim 1, wherein said sustained release composition is formulated as a spray.

8. The sustained release composition of claim 4, wherein said gelling agent is carboxymethyl cellulose or a salt thereof, xanthan gum, hydroxyethyl cellulose, hydroxymethyl cellulose, methyl cellulose, hydroxypropyl(methyl cellulose) or Poloxamer or any combination thereof.

9. The sustained release composition of claim 8, wherein said gelling agent is in an amount between about 1.0-2.5%.

10. The sustained release composition of claim 4 wherein the gelling agent includes carbomer.

11. The sustained release composition of claim 10 wherein the carbomer is in an amount of between about 0.6-4% w/w.

12. A sustained release composition comprising:

preformed silica microspheres 0.25-5.50% w/w that are impregnated with benzoyl peroxide such that there is also free benzoyl peroxide in the composition, wherein the composition comprises:

benzoyl peroxide 1-15% w/w;

gelling agent 0.6-4% w/w;

solvent 2-15% w/w;

sodium hydroxide to adjust pH; and water;

wherein the preformed silica microspheres were formed prior to being mixed with the benzoyl peroxide.

13. The sustained release composition of claim 12 wherein the gelling agent includes carbomer.

14. The sustained release composition of claim 12 wherein the solvent is selected from the group consisting of isopropanol, oleic acid, glycerol monooleate, oleyl alcohol, propylene glycol, isopropyl myristate, and combinations thereof.

15. The sustained release composition of claim 12 wherein the solvent is or includes propylene glycol.

16. A sustained release composition for topical application of pharmaceuticals comprising:

preformed silica microspheres added to benzoyl peroxide, wherein the preformed silica microspheres are impregnated with a first portion of benzoyl peroxide and a second portion of benzoyl peroxide is free in the composition, wherein the composition comprises at most a total of 10 percent by weight benzoyl peroxide and silica in an amount between 0.20-5.50% w/w, and wherein said composition is formulated for sustained release of said benzoyl peroxide;

wherein the preformed silica microspheres were formed prior to being mixed with the benzoyl peroxide.

17. A sustained release composition for topical application of pharmaceuticals comprising:

at most 10 percent by weight benzoyl peroxide;

preformed silica microspheres formed before contact with the benzoyl peroxide, the silica being present in the composition in an amount between 0.20-5.50% w/w;

wherein some of the benzoyl peroxide is impregnated into the preformed silica microspheres and some of the benzoyl peroxide is free in the composition;

wherein said composition is formulated for sustained release of said benzoyl peroxide from the preformed silica microspheres.

18. The sustained release composition of claim 1, wherein the benzoyl peroxide, mixed with the preformed silica microspheres, is in a polar solvent.

19. The sustained release composition of claim 18, wherein the solvent is ethoxydiglycol.

* * * * *